United States Patent [19]
Morris

[11] Patent Number: 6,106,523
[45] Date of Patent: Aug. 22, 2000

[54] IMPLEMENTS WITH COMPOSITE COATING

[75] Inventor: James R. Morris, Sedalia, Colo.

[73] Assignee: Medicor Corporation, Vernon Hills, Ill.

[21] Appl. No.: 09/246,630

[22] Filed: Feb. 8, 1999

[51] Int. Cl.⁷ .................................................. A61B 18/18
[52] U.S. Cl. .................................. 606/45; 606/41; 606/49
[58] Field of Search .................................. 606/41, 45, 49, 606/33

[56] References Cited

U.S. PATENT DOCUMENTS

| | | |
|---|---|---|
| 4,681,105 | 7/1987 | Tritt . |
| 5,380,320 | 1/1995 | Morris ........................................ 606/33 |
| 5,382,247 | 1/1995 | Cimino et al. ............................. 606/33 |
| 6,030,381 | 2/2000 | Jones et al. ................................ 606/41 |

*Primary Examiner*—Linda C. M. Dvorak
*Assistant Examiner*—Roy Gibson
*Attorney, Agent, or Firm*—Olson & Hierl, Ltd.

[57] ABSTRACT

An exceptionally durable insulating coating for surgical instruments and other implements is provided. The coating is a ceramic and polyurethane composite, and exhibits excellent insulative properties in the 500 KHZ to 1 MHZ frequency range. The ceramic coating can be readily applied by plasma deposition techniques. A polyurethane over coating is applied over the ceramic coating and is obtained using a polyester-based aliphatic polyurethane composition.

15 Claims, 3 Drawing Sheets

IMPLEMENTS WITH COMPOSITE COATING

FIELD OF THE INVENTION

This invention relates to implements such as tools and instruments. More particularly, this invention relates to surgical instruments provided with a composite ceramic and aliphatic polyurethane coating.

Background of the Invention

Since the inception of the monopolar and bipolar electro-surgical instruments for cutting and coagulating tissues, numerous cases of inadvertent and unwanted electrical shocks and burns to the patient and physician, and even deaths to patients, have been reported. In a great number of these reports, the cause of the reported injury was specified as resulting from the breakdown of the electro-surgical instrument's insulation.

The insulation material typically utilized has been poly (tetrafluoroethylene) (Teflon®), poly(vinyl chloride) (PVC), or heat-shrinkable plastic materials. While these materials do have exceptionally well-documented electrical insulative characteristics, they are severely lacking as ideal insulators for surgical instruments. The primary reasons for this are that they have very little abrasion resistance (i.e., the coating wears off easily). In addition, they can be scratched easily, leaving areas with bare metal exposed. They degrade rapidly with various sterilization methods, causing insulative properties to deteriorate; and additionally, they can retain moisture between bare metal and insulation, thus contributing to problems of corrosion and to problems with sterilization.

Also, they have low resistance to heat. The insulation degrades with heat generated by wattage flowing through the instrument during prolonged use. Finally, the currently utilized instrument insulations must be replaced regularly which results in excessive costs to health care providers.

Aliphatic polyurethanes are polyurethanes based on aliphatic isocyanates and mostly polyester and/or acrylic polyols. The chemical bonds in the more rigid systems are highly cross-linked to each other to create hard, dense systems that have very good chemical and moisture resistance. The rigid systems usually have excellent adhesion. 100% solids aliphatic polyurethane coatings offer very unique handling, performance and environmental advantages. 100% solids have zero or near zero volatile organic compound (VOC) emissions, set at virtually any temperature, are non-flammable, self-priming and set in minutes. Also, 100% solids have superior adhesion without using any primer. They are also resistant to chemical attack, gouging and abrasion. Further, they are flexible, impermeable and resilient.

It has now been found that a combined ceramic and aliphatic polyurethane coating on implements provides outstanding impact and abrasion resistance, as well as excellent dielectric properties, particularly in the 500 KHZ to 1 MHZ frequency range which is typical of electrosurgery unit generators. The composite coating is chemically inert and sterilizable, non-toxic, non-irritating, and non-cytotoxic, and thus can be used in contact with human tissue. The coating adheres well to the base metal of the implement, and thus minimizes corrosion and sterility problems. The coating is cost effective and is unaffected by various sterilization techniques. The coating is also readily applicable to a variety of shapes and sizes of implements such as surgical instruments, tools, corona printing rolls, and the like.

SUMMARY OF THE INVENTION

An implement such as a tool or a surgical instrument having excellent electrical insulative properties comprises a roughened metal substrate, a durable, continuous, thermally sprayed ceramic coating in contact with the metal substrate, and a polyester-based aliphatic polyurethane coating over the ceramic coating. This composite coating has a dielectric strength greater than 3,000 volts/mm in the frequency range of 500 KHZ to 1 MHZ, a metallographic porosity of less than one volume percent, and exhibits excellent abrasion resistance. The metal substrate preferably is stainless steel or titanium, and has a round transverse cross-section. The composite coating has a Young's Modulus value of no more than about $30 \times 10^6$ pounds per square inch parallel to the coating plane and a Young's Modulus anisotropy coefficient of at least about 2.

Implements that embody the present invention achieve the foregoing characteristics by utilizing a composite coating constituted by a thermally sprayed ceramic coating and an aliphatic polyurethane overcoating. The polyurethane overcoating is at least about 1 mil thick, preferably at least about 2.5 mils thick. Unlike molded and sintered ceramics such as ceramic insulating panels or wafers, thermally sprayed ceramic coatings are relatively more flexible and are characterized by anisotropic elastic properties. That is, the elastic properties of the resulting material determined parallel to the coating plane are different from those determined perpendicular to the coating plane. See, for example, Nakahira et al., "Anisotropy of Thermally Sprayed Coatings," Proceedings of the International Thermal Spray Conference and Exposition, Orlando, Fla., USA, 28 May-5 June 1992, pp. 1011–1017.

DESCRIPTION OF PREFERRED EMBODIMENTS

Figure 1:
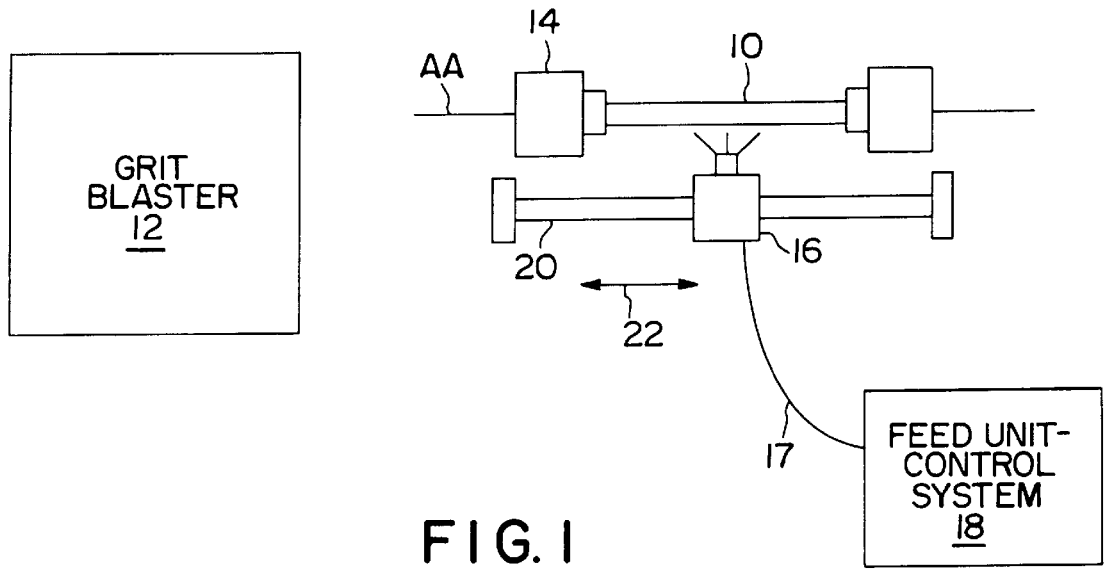
FIG. 1 is a schematic illustration of apparatus for applying a ceramic coating to an implement such as an electro-surgical instrument.

The particular ceramic of choice for the present thermal spray coatings on a roughened metal substrate such as steel, stainless steel, or titanium substrate, is $Al_2O_3$ (aluminum oxide), although mullite, magnesium oxide, zirconia-yttria, zirconia-calcia, or the like can also be utilized. The $Al_2O_3$ coating material has an inherently greater dielectric strength and, therefore, allows a relatively thinner coating to achieve the same insulative capacity as the other commonly used materials when applied as a relatively thicker coating.

Additionally, in contradistinction to molded ceramic panels, thermal spray coatings are more elastic, i.e., have a relatively lower Young's Modulus[1], that permits the use of such coatings on flexible or flexing parts of electrosurgical instruments.

[1] The well known Young's Modulus is defined as the ratio of stress to strain in the elastic range of the material. The higher the Young's Modulus of a material, the stiffer is that material.

The presently contemplated implements are first provided with an anisotropic, thermally sprayed ceramic coating that exhibits a Young's Modulus of no more than abut $30 \times 10^6$ pounds per square inches (psi), preferably no more than $15 \times 10^6$ psi, in a direction parallel to the coating plane. For the presently contemplated thermally sprayed ceramic coatings the Young's Modulus anisotropy coefficient is at least 2, and preferably is about 3. Particularly preferred thermally sprayed ceramic coatings for electrosurgical instruments are aluminum oxide coatings having a Young's Modulus of no more than about $15 \times 10^6$ pounds per square inch and a Young's Modulus anisotropy coefficient of about 3.

The preferred thickness of the ceramic coating for most surgical instrument applications has been found to be 0.01 to 0.015 inch. Coatings in this thickness range have been tested and found to be excellent insulators up to at least 4–6 kilovolts, 3,000–4,000 volts alternating current RMS. Relatively thinner or relatively thicker coatings can also be applied depending upon the particular ceramic material being used.

DC current leakage at 3,000 volts has been tested and found to be less than 100 micro amperes.

Coatings of $Al_2O_3$ have been tested and found to be non-toxic, non-cytotoxic, and non-irritating.

The applied ceramic coating has also been found not to degrade through repeated sterilization methods of chemical soak, steam and autoclave sterilization.

This ceramic coating has also been tested for wear and abrasion tested by placing coated samples in a rock tumbler device for 24 hours. This is roughly equivalent to 3–4 hours on a grinding wheel. The results of this test indicated that less than 1/1000 of an inch of coating material was removed.

Further tests designed to indicate the coating's resistance to scratching and nicking have been performed through purposeful and continual scratching and cutting of the coating with stainless steel scalpel blades and scissor blades. Because the $Al_2O_3$ coating is so much harder than the typical stainless steel, no cuts or scratches were obtained. Instead, the metal of the stainless steel blades was worn off by the coating.

The so produced ceramic coating is thereafter provided with an aliphatic polyurethane overcoat as will be discussed in greater detail hereinbelow.

The characteristics of the resulting composite ceramic-aliphatic polyurethane coating lead to significant cost savings to users.

In addition, due to the combination of ceramic and polyurethane characteristics, a significantly safer surgical instrument is produced. Hospital and physician risk are decreased as well.

FIG. 1 illustrates a method for providing a ceramic coating on a round stainless steel electro-surgical instrument 10, such as a reusable endoscopic electrode having a round shaft about 16 inches in length with a diameter of 0.065 inch.

Initially the instrument is masked to cover areas thereon which are not to be coated. The masking may be performed manually using conventional masking tape.

The instrument is next placed in a conventional grit blaster 12, such as, for example, that sold under the product designation Trinco Dry Blast Sand Blaster 36-BP2 which is commercially available from Trinity Tool Company, 34600 Commerce Road, Fraser, Minn. 48026. The surface of the instrument is cleaned and slightly roughened by the grit blaster prior to thermal spraying of the ceramic material.

The instrument is next mounted on a spindle assembly 14 with the longitudinal axis of the instrument coaxially aligned with the axis of rotation AA of the spindle assembly 14.

A coating applicator system which may comprise a plasma gun 16 connected by feed conduit 17 to material feed and control unit 18 is provided for spraying coating material in a plasma state onto the surface of the instrument. The coating applicator system may be an applicator system of a conventional type well known in the art such as, for example, that sold under the product designation Plasmatrong® Thermal Spray System Model #3700-$B_2$B-100-D which is commercially available from Miller Thermal, Inc., Plasmadyne and Mogul Products, 555 Communication Drive, P.O. Box 1081, Appleton, Wis. 54912. Coating material which is to be applied to an instrument 10 is initially placed in the material feed unit 18 in a powdered form. Powdered forms of the materials which may be used in the coating process, including aluminum oxide, an aluminum oxide and titanium dioxide mixture, and molybdenum are commercially available under the product designations AI-1010 F, AI-1070, and AI-1138, respectively, from Alloys International Products, 1901 Ellis School Road, Baytown, Tex. 77521.

The spindle assembly 14 is positioned with its axis of rotation AA parallel to a guide assembly 20 which is adapted to support plasma gun 16 thereon for reciprocal motion 22. The tip of the gun 16 may be positioned 3.5 in. from the surface of the instrument 10. In a typical application the gun may be reciprocated back and forth at an average speed of approximately 1 ft./sec. and the instrument may be rotated by the spindle about axis AA at a rate of approximately 250 revolutions per minute. Cooling air may be applied to the instrument as from adjacent air jet nozzles (not shown) to cool the coating material after it is applied to the instrument.

Figure 2:
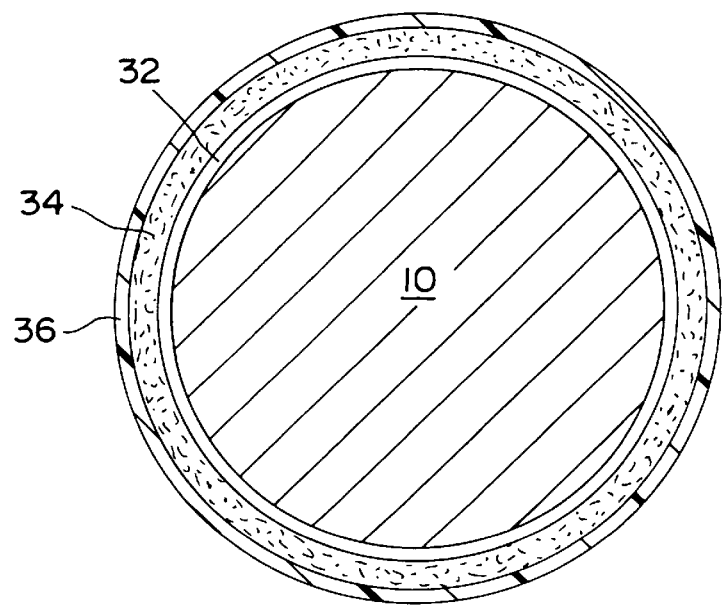
FIG. 2 is a cross-sectional view of an electro-surgical instrument with a composite coating which includes a ceramic layer and a polyester-based aliphatic polyurethane layer.

A coated instrument having the wear and insulating properties described elsewhere herein may be obtained through direct application of a single coating layer, such as a layer of aluminum oxide, to the instrument. In a preferred embodiment of the invention, however, shown in FIG. 2, three separate coatings are applied to the round shaft of the instrument: a bonding layer 32 (which may be molybdenum-powder #AI-1138 having a thickness of 0.001 in.), an insulative protection layer 34 (which may be aluminum oxide-powder #AI-1010 F having thickness of 0.020 in.), and an aliphatic polyurethane layer 36. The bonding layer 32 improves the bonding of the ceramic layer 34 to the instrument. The aliphatic polyurethane layer may be applied to ceramic layer 34 in one or more passes utilizing conventional spraying techniques.

Specific production parameters for the different ceramic powders listed above for use with the equipment described above are provided in Table 1, below.

TABLE 1

Parameters for Plasmatron ® Thermal Spray System

|  | Powder No. AI-1010F Sub-Sonic 40 KW | Powder No. AI-1138 Sub-Sonic 40 KW | Powder No. AI-1070 Sub-Sonic 40 KW |
|---|---|---|---|
| Operating Mode |  |  |  |
| Spray Gun | SG-100 | SG-100 | SG-100 |
| Anode | 2083-155 | 355 | 155 |
| Cathode | 1083A-112 | 112 | 112 |
| Gas Injector | 2083-113 | 113 | 113 |
| Nozzle # | N/A | N/A | N/A |
| Operating Parameters Power |  |  |  |
| Open Circuit Voltage | N/A | N/A | N/A |
| Operating Voltage | 34.6 | 42 | 40 |
| Operating Current | 900 | 800 | 800 |
| Arc Gas/Primary | Argon | Argon | Argon |
| Flow Rate | N/A | N/A | N/A |
| Critical Orifice No. | 56 | 56 | 56 |
| Press. Reg. $P_1$, psig | 50 | 50 | 50 |
| Auxiliary Gas/Secondary | Helium | Helium | Helium |
| Flow Rate | N/A | N/A | N/A |
| Critical Orifice No. | 80 | 80 | 80 |
| Press. Reg. $P_1$, psig | 100 | 100 | 100 |
| Powder Gas/Carrier | Argon | Argon | Argon |
| Flow Rate | N/A | N/A | N/A |
| Critical Orifice No. | 77 | 77 | 77 |
| Press. Reg. $P_1$, psig | 40 | 50 | 50 |
| Hopper Setting/RPM | 2.5 | 1.3 | 3.5 |
| Powder Port | N/A | N/A | N/A |
| Meter Wheel/RPM | 2.5 | 1.3 | 3.5 |
| Spray Distance | 3.5 in. | 3.5 in. | 3.5 in. |

In addition to the aforementioned plasma gun coating procedures, other coating procedures known in the ceramic arts such as detonation guns and high-velocity oxygen fuel systems could also be used. A plasma gun is currently the best mode contemplated for applying a coating, however.

When nonuniform articles are to be coated with the ceramic, the article may be held manually as with tongs and manually rotated and reciprocated in front of a ceramic applicator gun. Instruments coated with ceramic in the manner described above were tested and evaluated as described below. The same procedure as described above may be used to apply a coating of magnesium oxide, zirconia-yttria, or zirconia-calcia rather than aluminum oxide to form an insulative coating. The durability is first evaluated. Samples of a ceramic composite coating are processed in a rock tumbler device for 25 hours. This amount of wear is roughly equivalent to the wear which would be produced by 3–4 hours on a grinding wheel. The ceramic coating was not chipped or cracked after this treatment. From visual analysis under high magnification, it can be estimated that less than 1/1000 of an inch of coating material is removed during the experiment. The toxicology is next studied. The results of toxicological evaluation of coated stainless steel samples are shown in Table 2, below.

TABLE 2

| Toxicology Results | |
|---|---|
| Percent inhibition of cell growth QCOP L300 | Non-inhibitory |
| Medium eluate method QCOP L305 | Non-cytotoxic |
| Agar overlay QCOP L303 | Non-cytotoxic |
| USP intracutaneous irritation | |

TABLE 2-continued

| Toxicology Results | |
|---|---|
| QCOP B309 | |
| Normal saline extract | Non-irritating |
| Cottonseed oil extract | Non-irritating |
| USP mouse systemic injection QCOP B305 | |
| Normal saline extract | Non-toxic |
| Cottonseed oil extract | Non-toxic |
| Rabbit subcutaneous implantation | Non-irritating |

Electrical insulative properties are next considered. Table 3, below, illustrates the properties of the electrical insulative coating.

TABLE 3

Physical Properties of the Electrical Insulative Coating

| Application | Two coat plasma deposition |
|---|---|
| Insulative capacity | Greater than 3,000 V/mm |
| MOHS Hardness Scale (Diamond hardness = 10.0) | 9.2 |
| Tensile bond strength (psi) | >8,000 |
| Modulus of rupture (psi) | 19,000 |
| Modulus of elasticity ($10^6$ psi) (parallel to coating plane) | 11 |
| Density (q/cm$^3$) | 3.6 |
| Metallographic porosity (volume %) | <1 |
| Surface Finish As-coated (microinch rms) | 150 |

After the ceramic coating or layer has been applied to an implement, as described hereinabove, a polyester-based aliphatic polyurethane overcoat is applied, also by spraying. Conventional polyurethane spraying techniques can be utilized. The applied polyurethane coating is then cured at ambient or elevated temperatures, as desired.

Preferably, the ceramic coating is first tested to insure that there are no pinholes. The ceramic surface is then cleaned. Soaking in ethanol followed by an ultrasonic cleaning is a preferred procedure. The polyester-based aliphatic polyurethane coating is then sprayed onto the surface of the cleaned ceramic coated implement and cured. The polyester-based polyurethane coating is at least about 1 mil thick, more preferably at least about 2.5 mils thick.

A two component polyurethane, polyurea or polyurethane/polyurea hybrid can be utilized to form the overcoat. The two components are maintained separately until application. A spray gun is used to create the coating, mixing together the two polymer components just prior to exiting the spray gun. The polyurethane composition reaches its gel point almost immediately upon contact with the ceramic coating. The applied composition is then cured to form the overcoat.

The aliphatic polyurethane can applied in liquid form in one or more coats. Each coat is allowed to gel and cure to form the overcoat before the next one is applied.

Suitable aliphatic polyurethane coatings have been prepared by reacting an aliphatic isocyanate prepolymer, such as a prepolymer based on 1-isocyanato-3,3,5-trimethyl-5-isocyanatomethylcyclohexane, with a polyester polyol together with a aromatic diamine, such as the aromatic diamines described in U.S. Pat. No. 4,218,543 to Weber et al. The reaction mixture produces an elastomeric polyurethane coating which is substantially solvent-free, or has a relatively low solvent content.

The aliphatic polyisocyanate suitable for present purposes can be a trimerized or a biuret aliphatic such as a polymethylene polyisocyanate and, more particularly, a trimerized or biuret hexamethylene diisocyanate. The polymethylene polyisocyanates have free NCO groups or combinations of the trimerized and biuret polyisocyanates and typically up to about 35 percent by weight of the free NCO groups, such as for example from about 5 to 35 and more particularly 18 to 30 percent by weight of free NCO groups. The trimerized or biuret aliphatic prepolymers are prepared by reacting the selected polymethylene polyisocyanate in the presence of one or more catalysts to prepare the prepolymer reaction product. Trimerized or biuret products having high solid contents, for example 80 to 100 percent solids, with low viscosities, for example less than about 2500 cps and low odors, are preferred. If desired, small amounts of a solvent or diluent may be employed, such as for example small amounts (e.g., 25 percent by weight or less) of an aliphatic solvent. A combination of aliphatic and aromatic solvents may be employed, although it is not preferred.

Where a polyurethane prepolymer, or combinations thereof, has high viscosities (such as over 5000 cps) which makes mixing and pumping difficult, it has been found that the addition of a small amount of high boiling point, viscosity reducing organic compound reduces the viscosity and facilitates spraying. Such viscosity reducing compounds have a boiling point of about 140° C., or higher to avoid gassing during the polyurethane polymerization reaction. A hydrocarbon solvent is a preferred viscosity reducing substance for the present purposes. Particularly preferred are blended hydrocarbon solvents.

A wide variety of sprayable polyester-based aliphatic polyurethanes can be utilized for this purpose, including the so-called 100% solids polyurethanes, as long as the 100% solids polyurethane coating system is of adequate viscosity to be sprayed, with or without the use of a viscosity-reducing additive. The term "100% solids" as used herein means that the constituents of the ultimate coating are normally in a liquid state but convert to a solid film after application. If, for optimum sprayability, it is desired to reduce the viscosity of the sprayable coating system, a hydrocarbon solvent can be utilized for that purpose.

The 100% solids polyurethane coatings are made up of an isocyanate component and a polyester polyol component. A 100% solids polyurethane coating is an ASTM DI6 Type V polyurethane coating which is obtained when the isocyanate component is combined and reacts with the polyester polyol component, usually in the presence of a suitable catalyst. A metallic organo catalyst is used to form the polyurethane resin, usually about 0.001 to 0.2% by weight, based on the weight of the polyurethane resin is used. Typical catalysts are ferric acetyl acetonate, and dibutyl tin dilaurate. Ferric acetyl acetonate is preferred particularly in combination with a tertiary amine in a 3:1 molar ratio. Resilient polyurethane coatings that exhibit excellent impact and abrasion resistance, as well as dielectric strength are achievable in this manner. 100% solids aliphatic polyurethane coating systems are known in the art and are described, for example, by Guan, Journal of Protective Coatings and Linings, December 1995, pp. 74–81.

Also suitable for present purposes are aliphatic polyurethane prepolymers having a relatively low oligomer content and residual isocyanate content. In such systems, the use of a relatively viscous but relatively high molecular weight prepolymer as the isocyanate-rich component of the system and a relatively smaller amount of the polyester polyol, which has a relatively high solvent demand, can be utilized as the polyol-rich component of the system. See, for example Kramer et al., Paint and Coatings Industry, August 1994, p. 42.

A preferred aliphatic polyurethane resin is formed by reacting a fatty acid ester containing ultraviolet light absorbing groups and drying oil constituents with aliphatic diisocyanate.

In the solution process for making the fatty acid esters typical solvents that do not contain reactive hydrogen groups can be used. Illustrative are toluene, xylene, ketones such as methyl ethyl ketone, methyl isobutyl ketone, acetone and the like, ethylene glycol monoalkyl ether acetates, such as ethylene glycol monoethyl ether acetate, and the like.

Typical drying oil fatty acids that can be used to prepare the fatty acid esters are as follows: dehydrated castor oil fatty acids, soya oil fatty acids, tung oil fatty acids, linseed oil fatty acids, oiticica oil fatty acids, safflower oil fatty acids, and the like. Dehydrated castor oil fatty acids are preferred.

Typical polyols that can be used to prepare the fatty acid ester are as follows: glycerol, trimethylol alkanes, such as trimethylolethane, trimethylolpropane, and the like, pentaerythritol, methylglycoside, dipentaerythritol, and sorbitol. Trimethylol propane is preferred.

Typical monobasic organic acids that can be used to prepare the fatty acid ester are as follows: abietic acid, benzoic acid and p-tert-butylbenzoic acid.

One particularly preferred fatty acid ester that forms a high quality composition is the esterification product of dehydrated castor oil fatty acids/benzoic acid/trimethylol propane/dimethyl aminobenzoic acid and has a hydroxyl number of about 200 to 350.

Typical aliphatic diisocyanates that are used to form the polyurethane resin are as follows: propylene-1,2-diisocyanate, butylene-1,2-diisocyanate, butylene-1,3-diisocyanate, hexamethylene diisocyanate, octamethylene diisocyanate, nonamethylene diisocyanate, decamethylene diisocyanate, 2,11-diisocyanate-dodecane and the like; 2,2'-methylene-bis(cyclohexyl isocyanate), 3,3'-methylene-bis(cyclohexyl isocyanate), 4,4'-methylene-bis(cyclohexyl isocyanate), 4,4-ethylene-bis(cyclohexyl isocyanate), 4,4'-ethylene bis-(cyclohexyl isocyanate), 4,4'-propylene-bis-(cyclohexyl isocyanate), bis-(pura-isocyano-cyclohexyl) sulfide, bis(para-isocyano-cyclohexyl) sulfone, bis-(para-isocyanocyclohexyl) ether, bis-(para-isocyano-cyclohexyl) diethyl silane, bis-(para-isocyano-cyclohexyl) diphenyl silane, bis-(para-isocyano-cyclohexyl) ethyl phosphine oxide, bis-(para-isocyano-cyclohexyl) phenyl phosphine oxide, bis-(para-isocyano-cyclohexyl) N-phenyl amine, bis-(para-isocyano-cyclohexyl) N-methyl amine, 2,2-dimethyl propylene diisocyanate, 3-methoxy-hexamethylene diisocyanate, 2,5-dimethyl heptamethylene diisocyanate, 5-methyl-nonamethylene diisocyanate, 1,4-diisocyanocyclohexane, 1,2-diisocyano-octadecane, and the like.

One preferred aliphatic diisocyanate is 4,4' methylene bis (cyclohexyl isocyanate).

A capacitance, cosmetic, and mechanical evaluation was performed on aliphatic polyurethane plus ceramic coated stainless steel test samples after 20 cleaning/sterilization cycles. Additional cosmetic evaluations were performed after 40 and 60 cycles. The ceramic layer was aluminum oxide 10–12 mils thick, and the polyester based polyurethane overcoating (ISSC) was about 2.5–3.5 mils thick.

The cosmetic property analysis used test samples of which half were scratched on the surface and the others were not scratched. The samples were soaked in room temperature enzymatic cleaner solution for 15 minutes followed by an ambient temperature water rinse. The samples were then soaked in room temperature phenolic sterilizer solution for 10 minutes followed by an ambient temperature water rinse. In a live steam autoclave the samples were steam sterilized for 15 minutes at 273° F. Then for 10 minutes the samples were dried in an autoclave at 273° F. Finally, the samples were ultrasonically cleaned for 15 minutes in an ultrasonic sterilizer filed with room temperature distilled water. The procedure was repeated for 20 cycles and then the samples were evaluated. The samples were evaluated again after 40 and 60 cycles.

Figure 3:
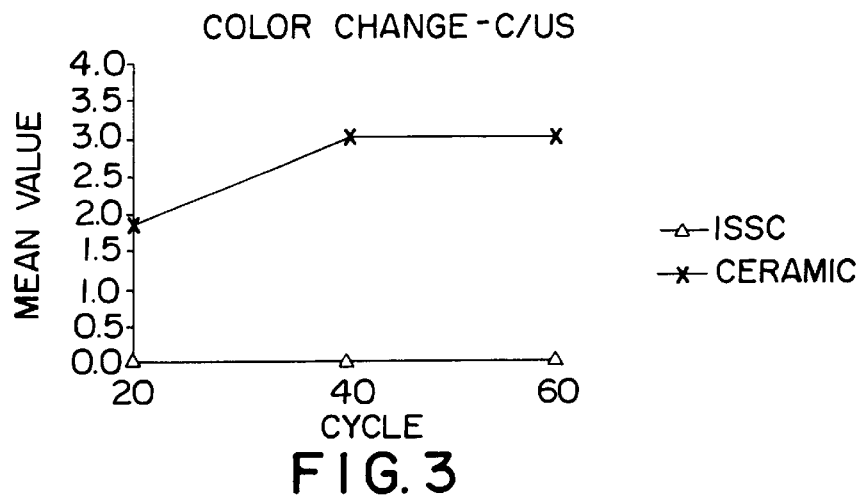
FIG. 3 is a graphical comparison of surface degradation exhibited by unscratched (C/US) ceramic surfaces and a polyester-based aliphatic polyurethane coated ceramic surfaces.
Figure 4:
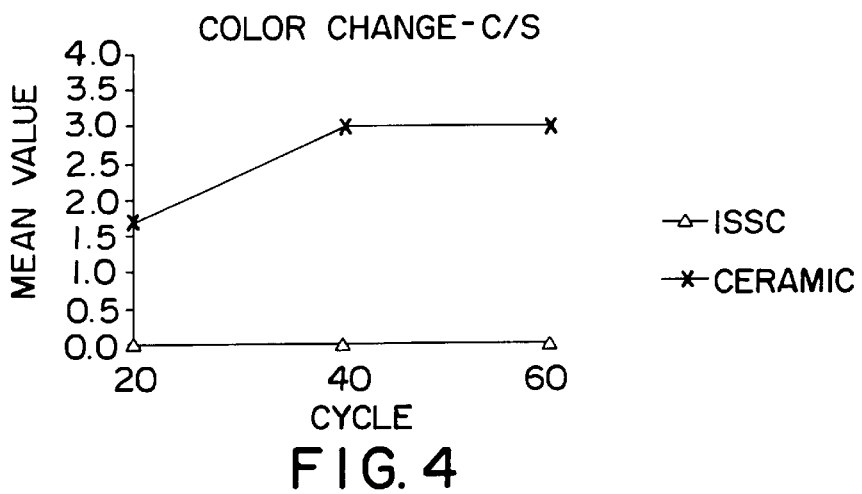
FIG. 4 is a graphical comparison of surface degradation exhibited by scratched (C/S) ceramic surfaces and a polyester-based aliphatic polyurethane coated ceramic surfaces.

Data gathered during the course of the experiment indicated that the aliphatic polyurethane coating, both scratched and non-scratched, provided significantly better resistance to cosmetic degradation caused by cleaning and sterilization processes than the ceramic coated samples. A graphical comparison of scores is shown in FIGS. 3 and 4.

The electrical property analysis was performed by a test which measured the capacitance/unit length of the insulation on a stainless steel insulated laparoscopic instrument shaft.

Data gathered during the course of this experiment indicated that ceramic coated tools and instruments with an additional aliphatic polyurethane coating have a substantially lower capacitance than the instruments having only a ceramic coating. Prior to cycling, the capacitance of aliphatic polyurethane coated sample shafts measured 25.5 pF/cm for unscratched samples and 27.1 pF/cm for scratched samples. Meanwhile, the ceramic samples without an additional polymer topcoat had capacitance measurements of 66.5 nF/cm and 55.3 nF/cm. That was greater than 1000 times the capacitance of the aliphatic polyurethane coated set.

Figure 5:
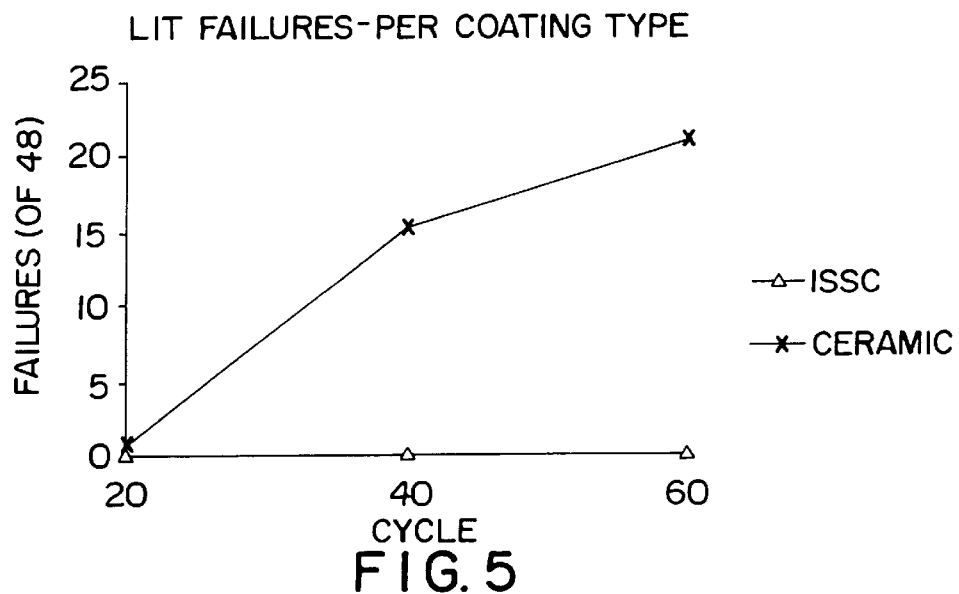
FIG. 5 is a graphical comparison of corona insulation and continuity tests (LIT tests) of ceramic coated samples and ceramic-and-aliphatic polyurethane coated metal samples.

A comparison of capacitance after cycling between the bare ceramic samples and the aliphatic polyurethane samples could not be performed due to cracks that had formed in the bare ceramic samples. The capacitance of the aliphatic polyurethane coated samples, however, was found to increase to 59.8 pF/cm for the scratched samples and 53.4 pF/cm for the unscratched samples. A graphical comparison of scores is presented in FIG. 5.

A mechanical property analysis simulated forceful impact between the ceramic coating material and other hard objects normally present in the hospital environment such as stainless steel surgical instruments. Various surgical instruments were placed into a utility mixer along with the test samples. The utility mixer was then rotated at 31 rpm for 3 hours.

Figure 6:
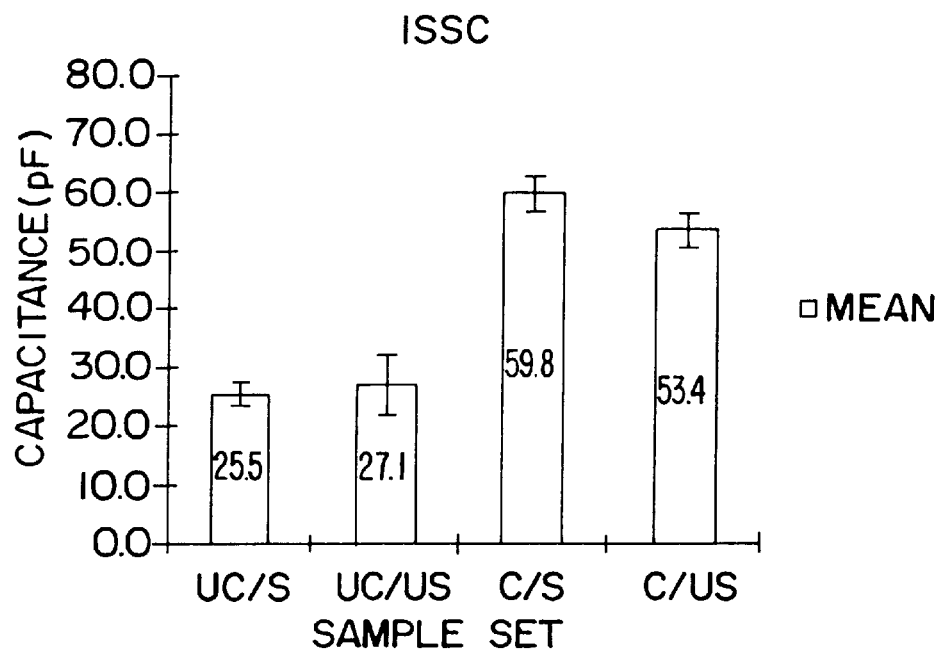
FIG. 6 is a graphical presentation of capacitance data for ceramic-and-aliphatic polyurethane coated metal samples.
Figure 7:
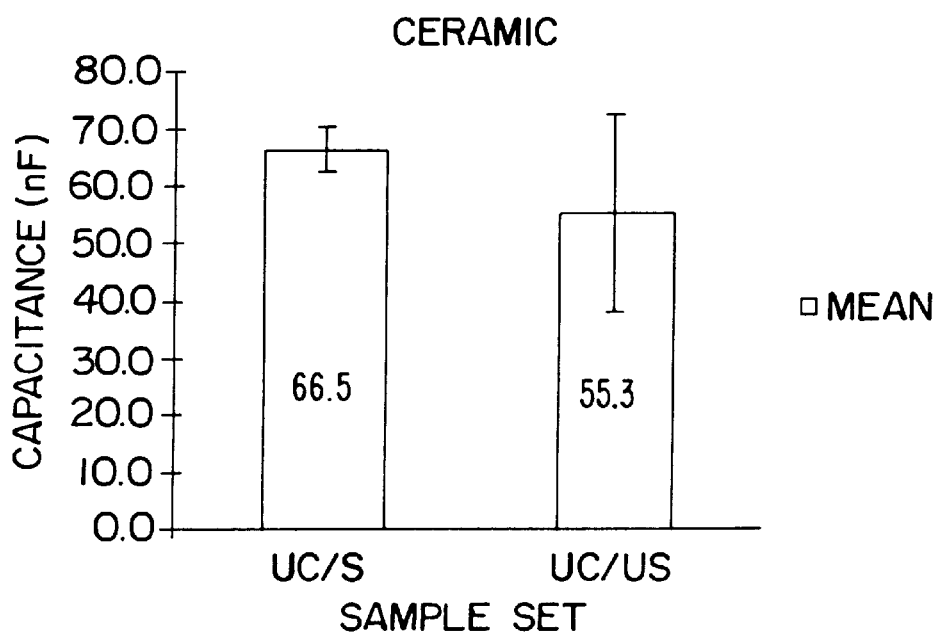
FIG. 7 is a graphical presentation of capacitance data for ceramic coated metal samples.

All of the polyester-based aliphatic polyurethane coated samples resisted the damage of the mechanical tumbling test significantly better than the samples coated with ceramic only. The ceramic coated samples revealed numerous cracks in the ceramic samples in both the scratched and unscratched sample sets while the aliphatic polyurethane coated samples were found to be pinhole-free in a post-tumbling LIT test. A graphical comparison of scores is shown in FIGS. 6 and 7.

While illustrative and presently preferred embodiments of the invention have been described in detail herein, it is to be understood that the inventive concepts may be otherwise variously embodied and employed and that the appended claims are intended to be construed to include such variations insofar as limited by the prior art.

I claim:

1. An implement which comprises:
   (a) a roughened metal substrate;
   (b) a thermally sprayed ceramic coating on the roughened metal substrate; and
   (c) a polyester-based aliphatic polyurethane coating over the thermally sprayed ceramic coating.

2. The implement in accordance with claim 1 wherein the ceramic is selected from the group consisting of aluminum oxide, mullite, magnesium oxide, zirconia-yttria and zirconia-calcia.

3. The implement in accordance with claim 1 wherein the aliphatic polyurethane is a reaction product of a polyester polyol and 4,4'-methylene-bis(cyclohexyl isocyanate).

4. The implement in accordance with claim 1 wherein the aliphatic polyurethane coating is at least about 1 mil thick.

5. A surgical instrument comprising:
   (a) a roughened stainless steel substrate;
   (b) a durable, continuous thermally sprayed ceramic coating on said roughened stainless steel substrate, said coating providing electrical insulative properties to said substrate in the 500 KHZ to 1 MHZ frequency range greater than 3,000 volts/mm and having a metallographic porosity of less than one volume percent; said thermally sprayed ceramic coating having a Young's Modulus of no more than about $30 \times 10^6$ pounds per square inch parallel to the coating plane, and a Young's Modulus anisotropy coefficient of at least about 2; and
   (c) an aliphatic polyester polyurethane coating over said thermally sprayed ceramic coating.

6. The instrument of claim 5 wherein said ceramic is selected from the group consisting of aluminum oxide, mullite, magnesium oxide, zirconia-yttria and zirconia-calcia.

7. The instrument of claim 5 wherein the thickness of said ceramic coating is about 0.01 to about 0.03 inch.

8. The instrument of claim 5 wherein a molybdenum bonding layer is present between said substrate and said ceramic coating.

9. The instrument of claim 5 wherein said aliphatic polyester polyurethane coating over said ceramic coating is at least about 1 mil thick.

10. The instrument of claim 5 wherein said aliphatic polyester polyurethane coating over said ceramic coating is at least about 2.5 mils thick.

11. The instrument of claim 5 wherein said roughened steel substrate has a round transverse cross-section.

12. A method of providing a durable insulating coating on a metal substrate which comprises:

(a) providing a roughened surface on the metal substrate;

(b) depositing on the roughened surface, by thermal spraying, a continuous ceramic coating having substantially uniform thickness sufficient to provide an insulative capacity of at least about 3000 volts/millimeter;

(c) thereafter applying over the ceramic coating a polyester-based aliphatic polyurethane composition; and (d) curing the applied aliphatic polyurethane composition.

13. The method in accordance with claim 12 wherein the polyester-based polyurethane composition is applied by spraying.

14. The method in accordance with claim 13 wherein the polyester-based aliphatic polyurethane composition is admixed prior to spraying with a hydrocarbon solvent to reduce the viscosity of the composition.

15. The method in accordance with claim 12 wherein the polyester-based aliphatic polyurethane composition is applied over the ceramic coating in an amount sufficient to provide an aliphatic polyurethane layer at least about 1 mil thick after curing.

* * * * *